(12) United States Patent
Yomtov

(10) Patent No.: US 8,948,880 B2
(45) Date of Patent: Feb. 3, 2015

(54) INTEGRATED SWITCHING CIRCUIT AND PULSE GENERATOR IN A NEUROSTIMULATOR LEAD

(71) Applicant: AdvaStim, Inc., Beverly, MA (US)

(72) Inventor: Barry M. Yomtov, Marblehead, MA (US)

(73) Assignee: AdvaStim, Inc., Beverly, MA (US)

( * ) Notice: Subject to any disclaimer, the term of this patent is extended or adjusted under 35 U.S.C. 154(b) by 0 days.

(21) Appl. No.: 13/796,636

(22) Filed: Mar. 12, 2013

(65) Prior Publication Data

US 2013/0245733 A1    Sep. 19, 2013

Related U.S. Application Data

(60) Provisional application No. 61/611,419, filed on Mar. 15, 2012.

(51) Int. Cl.
*A61N 1/05* (2006.01)
*A61N 1/375* (2006.01)
*A61N 1/36* (2006.01)

(52) U.S. Cl.
CPC .............. *A61N 1/05* (2013.01); *A61N 1/3758* (2013.01); *A61N 1/36125* (2013.01)
USPC ........................................................ 607/116

(58) Field of Classification Search
CPC .... A61N 1/05; A61N 1/36125; A61N 1/3758
USPC ................................................. 607/115–116
See application file for complete search history.

(56) References Cited

U.S. PATENT DOCUMENTS

| 7,957,818 | B2 | 6/2011 | Swoyer |
| 2002/0065544 | A1* | 5/2002 | Smits ............................ 607/122 |
| 2009/0228071 | A1 | 9/2009 | Bourget |
| 2011/0034964 | A1* | 2/2011 | Bi et al. ............................ 607/5 |
| 2012/0296271 | A1 | 11/2012 | Yomtov et al. |

FOREIGN PATENT DOCUMENTS

| WO | 03092807 | 11/2003 |
| WO | 2006029090 | 3/2006 |

OTHER PUBLICATIONS

International Search Report and Written Opinion for PCT/US2013/031307; Nov. 19, 2013.

* cited by examiner

*Primary Examiner* — Rex R Holmes
(74) *Attorney, Agent, or Firm* — Bryan A. Santarelli; Lane Powell PC

(57) ABSTRACT

A stimulation lead for connecting a pulse generator having a plurality of outputs to electrodes of an electrode array includes a flexible body and the electrode array. The electrode array is distal to the flexible body and the flexible body has a proximal portion and an interface portion. A selection circuit within the interface portion has a plurality of inputs, each input of the selection circuit connected to an output of the pulse generator and a plurality of outputs, each output of the selection circuit being coupled to a respective one of the electrodes of the electrode array. The plurality of outputs of the selection circuit are greater in number than the plurality of outputs of the pulse generator.

12 Claims, 5 Drawing Sheets

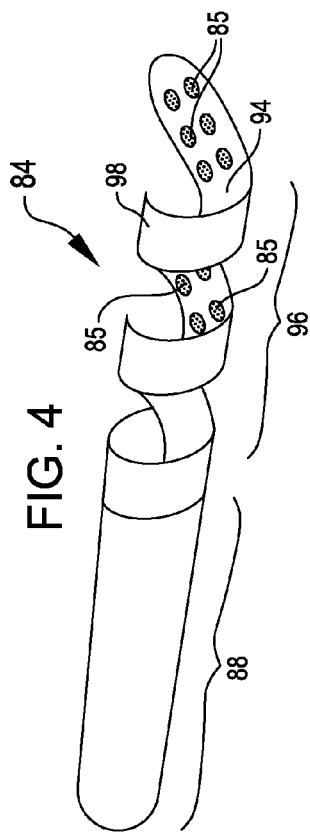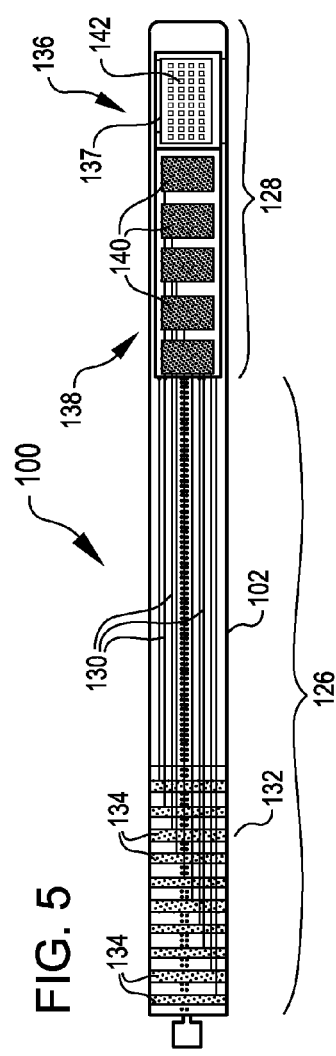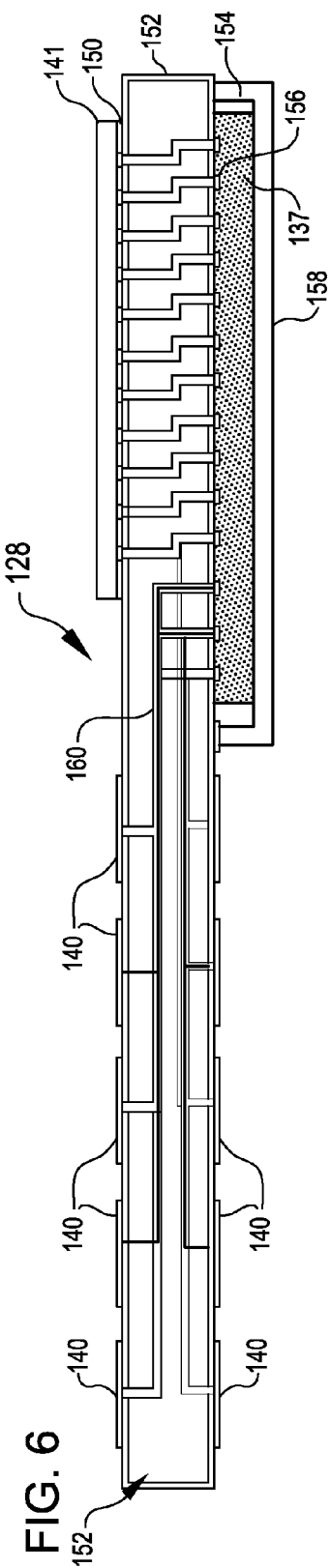

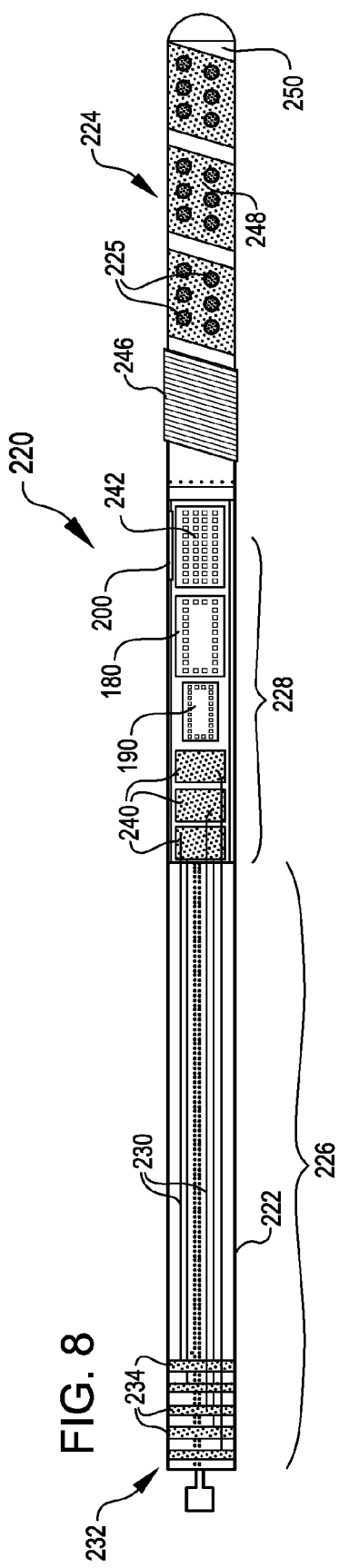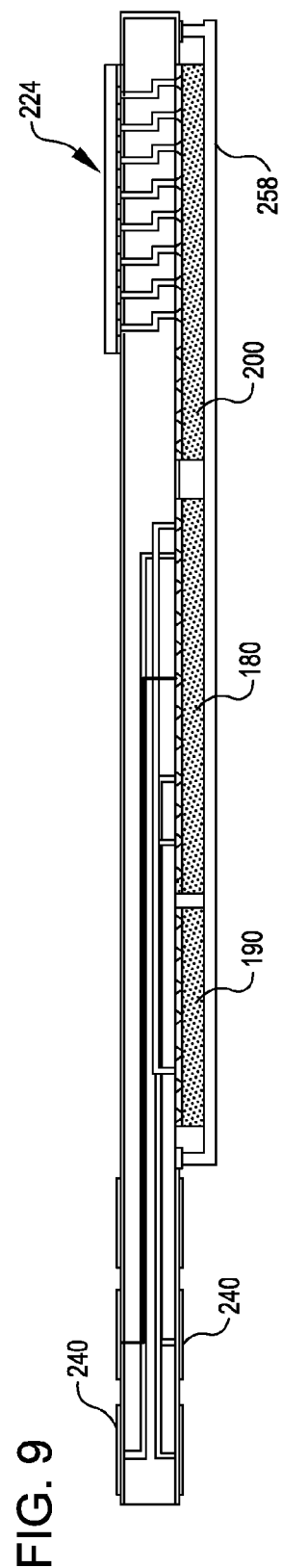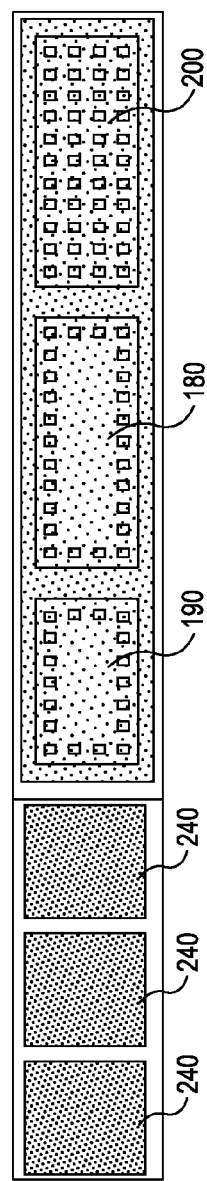
FIG. 8
FIG. 9
FIG. 10

INTEGRATED SWITCHING CIRCUIT AND PULSE GENERATOR IN A NEUROSTIMULATOR LEAD

PRIORITY CLAIM

The present application claims the benefit of U.S. Provisional Patent Application Ser. No. 61/611,419 filed Mar. 15, 2012, which application is incorporated herein by reference in its entirety.

BACKGROUND

The present invention generally relates to a lead for use in an implantable therapy system. The present invention more particularly relates to a stimulator lead having an integrated switching circuit and optionally also having an integrated pulse generator for efficiently providing an array of electrodes with stimulation energy from an implantable pulse generator.

Implantable therapy delivery systems have been in the art and in commercial use for decades. Such systems include cardiac rhythm management systems such pacemakers and defibrillators, nerve stimulators, and even drug delivery systems.

Such therapy systems, and especially in the case of cardiac rhythm management and nerve stimulator systems, include an implantable device that includes a power source, such as a battery and electronic circuitry that generates therapy stimulation pulses and controls when the therapy stimulation pulses are delivered. To actually deliver the stimulation pulses, the systems also generally include multiple stimulation electrodes on the surface of a lead that make electrical contact with the desired (target) tissue and a lead system, including one or more leads that connect the electrodes to the electronic circuitry in the device.

As implantable therapy device design has progressed over time, more and more functionality has been incorporated into the implantable devices and more and more electrodes have been similarly required to shape stimulation at the target tissue volume to enable that functionality. For example, implantable therapy devices usually now incorporate microcontrollers that are capable of controlling multiple therapy delivery modalities in multiple locations of the body. Those modalities may include both stimulation pulse delivery to selected tissue(s) and/or physiologic activity monitoring and data gathering for analysis and adjustment of therapy. In the case of nerve stimulation systems, these systems now find use in various locations of the body as for example, in brain tissue stimulation and spinal nerve stimulation.

Particularly in nerve stimulators, there has been an increase in the number of electrodes assigned to shape and deliver electrical pulses to a given anatomical region. The intended advantage is to obtain stimulation selectivity and directionality and to shape current delivery to a volume of tissue. Today, a system may incorporate as many as sixteen to twenty electrodes in a given area. Unfortunately, current state of the art connectivity measures to connect the electrodes back to the implantable pulse generation devices have limited the number and utility of electrodes.

For example, each electrode requires an electrical conductor or wire to extend from the electrode through its associated lead and back to the implanted device. The large number of such conductors is limited by the amount of space available in a lead. Further, each conductor requires a hermetically sealed connection with the implanted device. This places a huge burden on feed-through systems which can accommodate only a limited number required contacts and in effect, limits the number of electrodes to the constraints imposed by the connector.

Standard technology includes conductor wire for lead catheters, torroidal spring connectors between the lead and the implantable pulse generator devices, and a hermetic feed-through constructed from metal pins and ceramic insulators. Alternative designs could include improvement to the technology for these methods of connecting the lead to the implantable pulse generator device, by providing higher density connections through miniaturization. Higher density electrodes may now be designed through the use of thin film deposition technology to establish higher density electrodes as well as the high density interconnect conductors.

Still further, the required higher density of conductors required for the increased number of electrodes results in smaller diameter conductors. The smaller diameter conductors present higher impedance conduction paths between the electrodes and the implantable devices. This results in higher required power output from the implantable electronic devices to deliver the desired effective stimulation therapy. The required higher power output also either decreases battery life of the implantable devices or requires larger batteries to be employed. The smaller diameter conductor wire would also exhibit reduced strength and flex life in locations where this results in reduced reliability of the cable lead. Such stresses at the lead/stimulator connections cause an unacceptably high rate of device failure.

As may be seen from the foregoing, there is a need in the art for a different approach in providing therapy within a body where electric therapy is delivered from an implantable pulse generator device to a high density of electrodes. It would be desirable if such an approach would avoid high impedance conduction paths, minimize electrode dislodgement, prevent interconnection issues and increase the safety to and convenience of the patient. The present invention addresses these and other issues.

SUMMARY

According to one embodiment, a stimulation lead for connecting a pulse generator having a plurality of outputs to electrodes of an electrode array includes a flexible body and the electrode array. The electrode array is distal to the flexible body and the flexible body has a proximal portion and an interface portion. The lead further includes a plurality of conductors extending through the proximal portion to the interface portion, a connector arranged to connect a proximal end of each one of the conductors to a respective given one of the outputs, and a selection circuit within the interface portion. The selection circuit has a plurality of inputs. Each input of the selection circuit is connected to a distal end of a respective given one of the conductors. The selection circuit further has a plurality of outputs. Each output of the selection circuit is coupled to a respective one of the electrodes of the electrode array. The plurality of outputs of the selection circuit are greater in number than the plurality of outputs of the pulse generator.

The electrode array may include a flexible substrate and the electrodes of the electrode array may be distributed and carried on the flexible substrate. The flexible substrate may be configured as a cylinder. The electrode array may include a flexible cylindrical carrier, and the flexible substrate may be wrapped about the flexible cylindrical carrier. The flexible cylindrical carrier may be formed of silicone. The flexible substrate may be substantially planar and have a paddle configuration.

The electrode array may include a backing layer arranged in a corkscrew configuration and the flexible substrate may be carried on the backing layer within the corkscrew configuration.

The selection circuit may include a switching array. The switching array may comprise an integrated circuit.

In another embodiment, a universal stimulation lead module for connecting a pulse generator having a plurality of outputs to electrodes of an electrode array includes a flexible body having a proximal portion and a distal interface portion, a plurality of conductors extending through the proximal portion to the interface portion, a connector arranged to connect a proximal end of each one of the conductors to a respective given one of the outputs, and a selection circuit within the interface portion. The selection circuit has a plurality of inputs, each input of the selection circuit being connected to a distal end of a respective given one of the conductors. The selection circuit further has a plurality of outputs, each output of the selection circuit being arranged to be coupled to a respective one of the electrodes of the electrode array. The plurality of outputs of the selection circuit are greater in number than the plurality of outputs of the pulse generator.

The selection circuit may include a switching array. The switching array may comprise an integrated circuit.

In another embodiment, a stimulation lead provides stimulation energy to selected ones of a plurality of electrodes of an electrode array under control of a control device having a plurality of outputs that provide power and control signals. The stimulation lead includes a flexible body and the electrode array. The electrode array is distal to the flexible body. The flexible body has a proximal portion and an interface portion. The lead further includes a plurality of conductors extending through the proximal portion to the interface portion, a connector arranged to connect a proximal end of each one of the conductors to a respective given one of the outputs and a pulse generator within the interface portion. The pulse generator is responsive to the power and control signals of the control device to generate the stimulation energy. The lead further includes a selection circuit also within the interface portion. The selection circuit is coupled to the pulse generator and further has a plurality of outputs. Each output of the selection circuit is coupled to a respective one of the electrodes of the electrode array. The selection circuit is arranged to provide selected ones of the electrodes with the stimulation energy responsive to the control signals from the control device. The plurality of outputs of the selection circuit are greater in number than the plurality of outputs of the control device.

The electrode array may include a flexible substrate and the electrodes of the electrode array may be distributed and carried on the flexible substrate. The flexible substrate may be configured as a cylinder. The electrode array may include a flexible cylindrical carrier, and the flexible substrate may be wrapped about the flexible cylindrical carrier. The flexible cylindrical carrier may be formed of silicone. The flexible substrate may be substantially planar and have a paddle configuration.

The electrode array may include a backing layer arranged in a corkscrew configuration. The flexible substrate may be carried on the backing layer within the corkscrew configuration.

The selection circuit may include a switching array. The switching array may comprise an integrated circuit. The pulse generator comprises an integrated circuit.

In still another embodiment a universal stimulation lead module provides stimulation energy to selected ones of a plurality of electrodes of an electrode array under control of a control device having a plurality of outputs that provide power and control signals. The lead module includes a flexible body having a proximal portion and a distal interface portion, a plurality of conductors extending through the proximal portion to the interface portion, a connector arranged to connect a proximal end of each one of the conductors to a respective given one of the outputs of the control device and a pulse generator within the interface portion. The pulse generator is response to the power and controls signals from the control device to generate the stimulation energy. The selection circuit is also within the interface portion and is coupled to the pulse generator. The selection circuit has a plurality of outputs, each output of the selection circuit being coupled to a respective one of the electrodes of the electrode array. The selection circuit is arranged to provide selected ones of the electrodes with the stimulation energy responsive to the control signals from the control device. The plurality of outputs of the selection circuit are greater in number than the plurality of outputs of the control device.

The selection circuit may include a switching array. The switching array may comprise an integrated circuit. The pulse generator comprises an integrated circuit.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 4 is a perspective view of the electrode array of the stimulation lead of FIG. 3 according to an embodiment of the invention;

FIG. 5 is a top view of a universal stimulation lead module according to an embodiment of the invention;

FIG. 6 is a sectional view of the interface portion of the universal stimulation lead module of FIG. 5;

FIG. 8 is a top view of a stimulation lead wherein the pulse generator is located on the stimulation lead according to a further embodiment of the invention;

FIG. 9 is a sectional view, to an enlarged scale, of the electronics module of the stimulation lead of FIG. 8;

FIG. 10 is a top view, to an enlarged scale, of the electronics module of the stimulation lead of FIG. 8.

DETAILED DESCRIPTION

Figure 1:
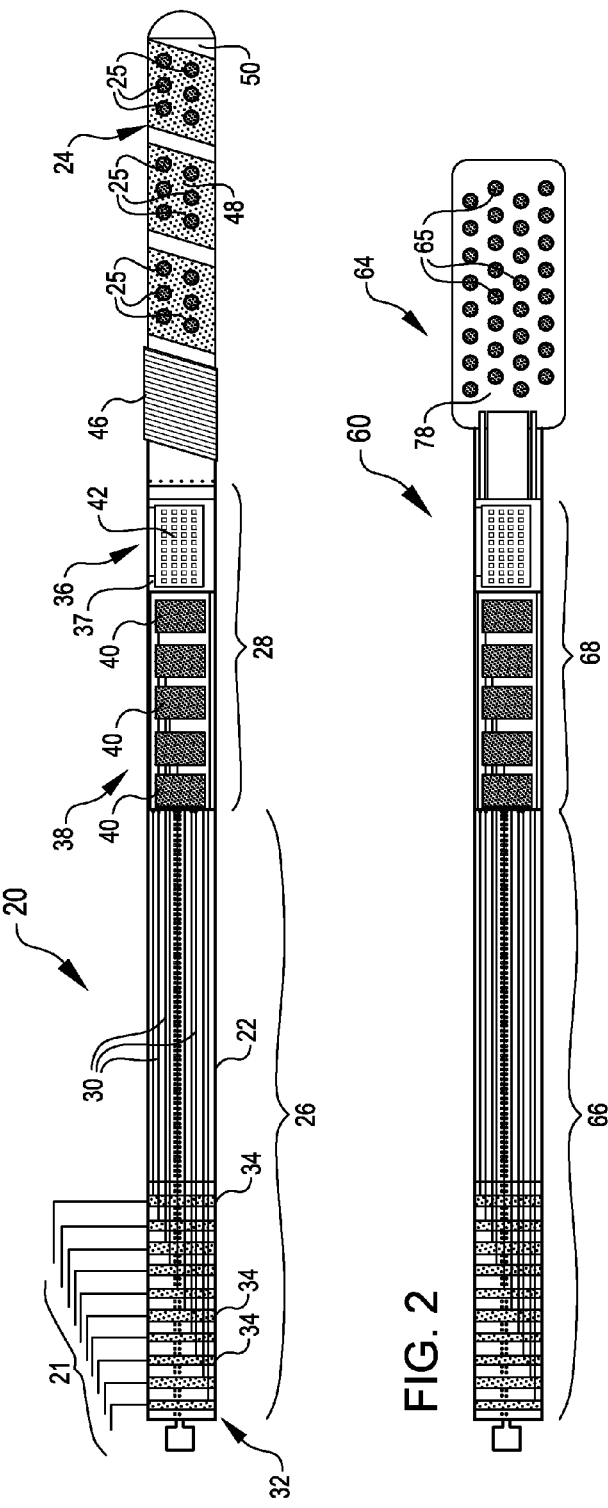
FIG. 1 is a top view of a stimulation lead according to one embodiment of the invention.

Referring now to FIG. 1, it is a top view of a stimulation lead according to one embodiment of the invention. The stimulation lead 20 of FIG. 1 is arranged for connecting a pulse generator having a plurality of outputs 21 to electrodes 25 of an electrode array 24. The stimulation lead 20 generally includes a flexible body 22 and the electrode array 24. The electrode array 24, which includes a plurality of electrodes 25, is distal to the flexible body 22. The flexible body 22 has a proximal portion 26 and an interface portion 28. The lead 20 further includes a plurality of conductors 30 extending through the proximal portion 26 to the interface portion 28. The lead 20 still further includes a connector 32 having contacts 34 associated with each of the pulse generator outputs 21. The contacts 34 are arranged to connect a proximal end of each one of the conductors 30 to a respective given one of the pulse generator outputs 21.

The lead 20 further includes a selection circuit 36 within the interface portion 28. The selection circuit 36 preferably includes an integrated switching array 37 of the type known in the art. The selection circuit 36 has a plurality of inputs 38 in the form of connection pads 40. Each of the connection pads 40 is connected to a distal end of a respective given one of the conductors 30. The selection circuit 36 further has a plurality of outputs 42. Each of the outputs 42 of the selection circuit 36 is coupled to a respective one of the electrodes 25 of the electrode array 24 by conductors 46. As may be noted in FIG. 1, the plurality of outputs 42 of the selection circuit are greater in number than the plurality of outputs 21 of the pulse generator.

The electrode array 24, in this embodiment, takes the form of electrodes 25 deposited on a flexible thin film substrate 48. The thin film substrate 48 is configured as a cylinder by being wrapped around a flexible rod 50 that may be formed from silicone, for example. The wrapping of the thin film electrode array around the silicone flexible rod 50 provides for improved reliability with lead flex and for improved maneuverability.

Figure 2:
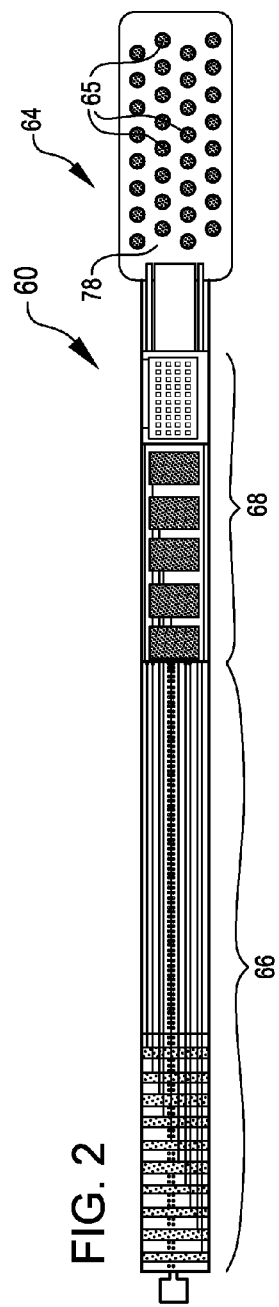
FIG. 2 is a top view of another stimulation lead according to another embodiment of the invention.

FIG. 2 is a top view of another stimulation lead 60 according to another embodiment of the invention. The lead 60 includes a proximal portion 66 and an interface portion 68 substantially identical to the proximal portion 26 and interface portion 28 of lead 20 of FIG. 1. However, here lead 60 includes an electrode array 64 of electrodes 65 deposited on a flexible substrate 78 to form the thin film electrode array 64 in a flat paddle and planar configuration. The electrode array 64 may have a silicone backing 78 to add to directionality, structure, and strength of the thin film electrode array. The paddle electrode configuration could also include a lead introducer catheter, of the type known in the art, to allow the electrode array to be curled up during deployment. Once the catheter is in place, the sheath may be withdrawn allowing the paddle to fold out and be optimally positioned in the desired space.

Figure 3:
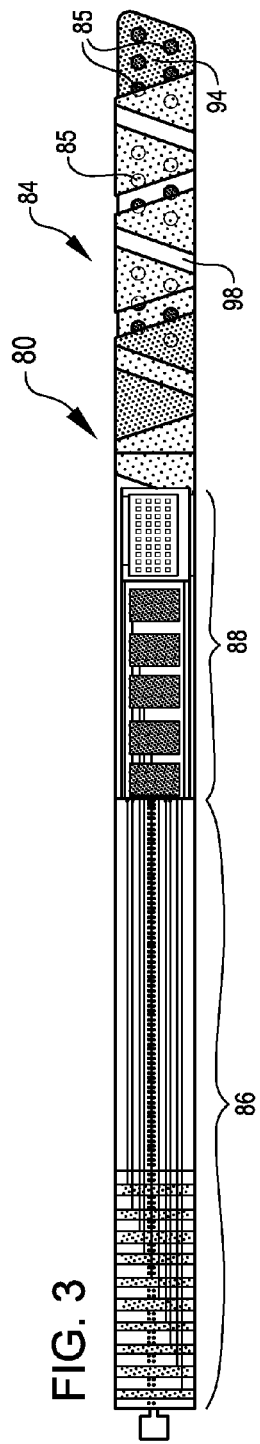
FIG. 3 is a top view of a further stimulation lead according to a further embodiment of the invention.

FIG. 3 is a top view of another stimulation lead 80 according to another embodiment of the invention. The lead 80 includes a proximal portion 86 and an interface portion 88 substantially identical to the proximal portion 26 and interface portion 28 of lead 20 of FIG. 1. However, as may be best seen in the perspective view of FIG. 4, the lead 80 includes an electrode array 84 of electrodes 85 deposited on a flexible substrate 94 that is carried on the inside of a spiraled silicone backing 98 to form the thin film electrode array 84 in a spiral configuration 96. This allows the cuff of the electrode array 84 to wrap about an individual nerve with the electrode surface facing the nerve. The silicone backing 98 adds to directionality, structure, and strength of the thin film electrode array 96.

FIG. 5 is a top view of a universal stimulation lead module 100 according to an embodiment of the invention. This provides a generic module for a customized electrode array to suit the needs of a specific clinical indication and anatomical site in need of electrical stimulation. More specifically, the universal stimulation lead module 100 of FIG. 5 may be employed for connecting a pulse generator (not shown) having a plurality of outputs to electrodes of an electrode array. In addition to a customized electrode array, the module 100 may also be used with any one of the electrode arrays disclosed herein. The lead module 100 includes a flexible body 102 having a proximal portion 126 and a distal interface portion 128. A plurality of conductors 130 extend through the proximal portion 126 to the interface portion 128. A connector 132 has a plurality of contacts 134. Each contact 134 is arranged to be connected to a respective given one of the outputs of the pulse generator. The conductors 130, in turn, connect each respective given one of the contacts 134 to a selection circuit 136 within the interface portion 128. The selection circuit 136 includes an integrated circuit switching array 137 and has a plurality of inputs 138 in the form of connection pads 140. Each of the connection pads 140 of the selection circuit 136 is connected to a distal end of a respective given one of the conductors 130. The selection circuit 136 further has a plurality of outputs 142. Each output 142 of the selection circuit 136 is arranged to be coupled to a respective one of the electrodes of an electrode array (not shown). The plurality of outputs 142 of the selection circuit 136 are greater in number than the plurality of outputs of the pulse generator and hence the connection contacts 134.

FIG. 6 is a sectional view of the interface portion 128 of the universal stimulation lead module 100 of FIG. 5. Here it may be seen that the interface portion 128 includes a plurality of layers 152 of a ceramic substrate 156. The integrated circuit 137 is electrically connected to the bottom side of the interface portion of the ceramic substrate 156. A titanium or ceramic lid 158 having a gold brazed flange 154 covers the integrated circuit 137 to provide a hermetically sealed enclosure. On top of the interface portion 128 is a thin film array 141 that includes the outputs 142 (FIG. 5) of the interface portion 128. Between the layers 152 of the ceramic are formed conductor paths 160 as, for example, path 160 to interconnect the connection pads 140 to the integrated circuit 137.

Both integrated circuit 137 and the thin film array 141 may be designed as a grid array for the interconnection process. The ceramic substrate 152 provides a hermetic interconnect between the integrated circuit 137 and external structures to which it will be electrically connected. Staggering the interconnections within the ceramic substrate 156 ensures a hermetic connection for the electrical connections 160.

Figure 7:
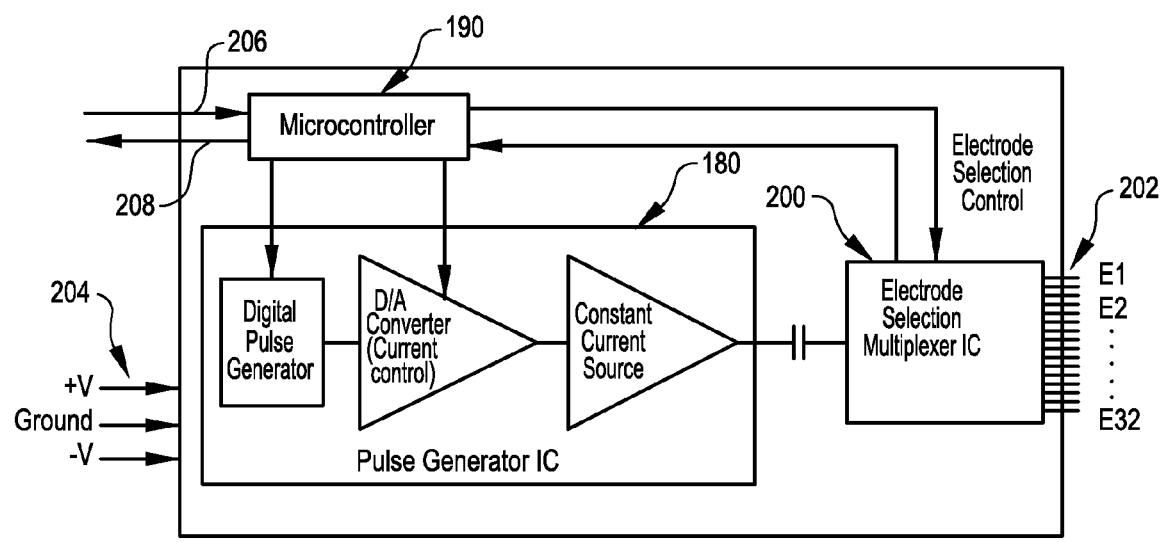
FIG. 7 is a circuit diagram of an alternative lead embodiment wherein the pulse generator is located on the stimulation lead according to another embodiment of the invention.

FIG. 7 is a circuit diagram of an alternative lead embodiment wherein the pulse generator 180 is located on the stimulation lead according to another embodiment of the invention. Along with the pulse generator 180, in accordance with this embodiment, a microcontroller 190 and an electrode selection integrated circuit 200 are also on the lead 100. A more specific example follows with respect to FIG. 8.

In FIG. 7 it may be seen that the microcontroller 190 is coupled to both the pulse generator 180 and electrode selection circuit 200. The microcontroller 180, responsive to received control signals generated by an implanted power source and control device, determines the parameters of the electrical stimulation provided by the pulse generator 180 and the electrodes to be selected by the electrode selection circuit 200 to which the electrical stimulation is to be applied. In FIG. 7, it may be seen that the electrode selection circuit 200 has for example 32 outputs 202 (E1-E32) while it has only three power inputs 204, one control input 206 and one control output 208 that extend to outside of the lead. Hence with just a few inputs, the lead is able to provide many more electrodes with stimulation. Each of the microcontroller 190, the pulse generator 180, and the selection circuit 200 may be a separate integrated circuit or may be integrated into one circuit.

Referring now to FIG. 8, it is a top view of a stimulation lead 220 wherein the pulse generator 180 is located on the stimulation lead 220 according to a further embodiment of the invention. FIG. 9 is a sectional view, to an enlarged scale, of the electronics module 228 of the stimulation lead 220 of FIG. 8 and FIG. 10 is top view, to an enlarged scale, of the electronics module 228 of the stimulation lead 220 of FIG. 8.

The stimulation lead 220 of FIGS. 8-10 provides stimulation energy to selected ones of a plurality of electrodes 225 of an electrode array 224 under control of a control device (not shown) having a plurality of outputs that provide power and control signals. The stimulation lead 220 includes a flexible body 222 and the electrode array 224. The electrode array 224 is distal to the flexible body 222. The flexible body 222 has a proximal portion 226 and an interface portion 228. The lead 220 further includes a plurality of conductors 230 extending through the proximal portion 226 to the interface portion 228. A connector 242 has a plurality of contacts 234 arranged to connect a proximal end of each one of the conductors 230 to a respective given one of the outputs. The lead 220 further includes the pulse generator 180, the microcontroller 190, and the electrode selection circuit 200 within the interface portion. The pulse generator 180 is responsive to the power and control signals of the control device to generate the stimulation energy. The electrode selection circuit 200 is coupled to the pulse generator 180 and further has a plurality of outputs 242. Each of the outputs 242 of the selection circuit 200 is coupled to a respective one of the electrodes 225 of the electrode array 224. The electrode selection circuit 200 is arranged to provide selected ones of the electrodes 225 with the stimulation energy responsive to the control signals from the control device. The plurality of outputs 242 of the selection circuit 200 are greater in number than the plurality of outputs of the control device (and thus the number of contacts 234).

The lead 220 may be fabricated in the same manner as that described with respect to FIG. 6. Also, the proximal portion 226 and interface portion 228 may be fabricated without an electrodes array so that together they may form a universal lead module having a pulse generator 180 therein for use with any desired electrode array. Further, as in the previous embodiments, the electrode array 224 may include a flexible substrate 248 and the electrodes 225 of the electrode array 224 may be distributed and carried on the flexible substrate 248. The flexible substrate 248 may be configured as a cylinder. The electrode array 224 may include a flexible cylindrical carrier 250, and the flexible substrate 248 may be wrapped about the flexible cylindrical carrier. The flexible cylindrical carrier 250 may be formed of silicone.

The electrode array 224 may include a backing layer as shown in the embodiment of FIGS. 3 and 4 arranged in a corkscrew configuration. The flexible substrate may be carried on the backing layer 98 within the corkscrew configuration.

Figure 11:
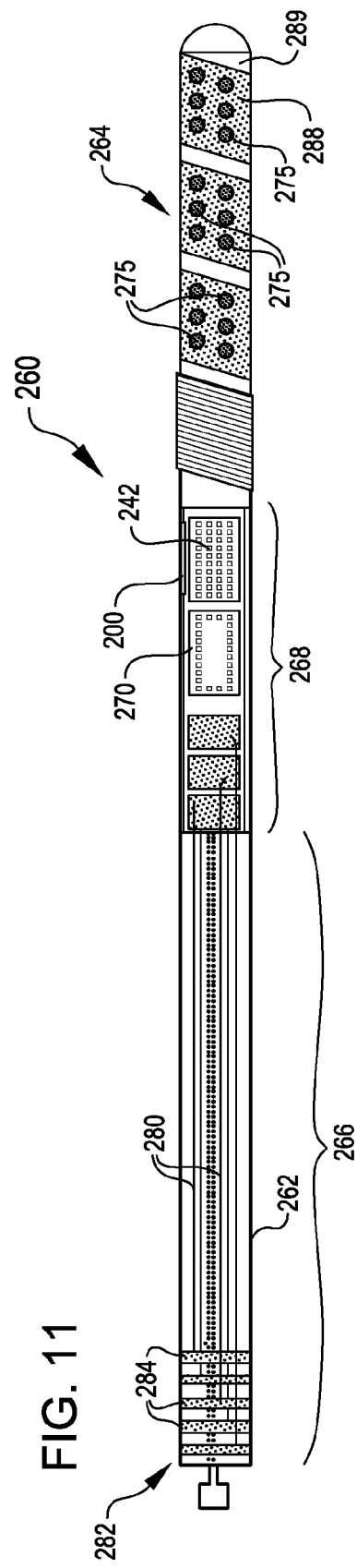
FIG. 11 is a top view of another stimulation lead wherein the pulse generator is located on the stimulation lead according to a further embodiment of the invention.

FIG. 11 is a top view of another stimulation lead 260 wherein the pulse generator 180 is located on the stimulation lead 260 according to a further embodiment of the invention. Here, both the pulse generator 180 and microcontroller 190 are integrated into a common integrated circuit 270. As in the previous embodiments, the stimulation lead 260 includes a flexible body 262 and an electrode array 264. The electrode array 264 is distal to the flexible body 262.

The flexible body 262 has a proximal portion 226 and an interface portion 228, which portions may be constructed and fabricated as previously described. To that end, the lead further includes a plurality of conductors 280 extending through the proximal portion 266 to the interface portion 268. A connector 282 has a plurality of contacts 284 arranged to connect a proximal end of each one of the conductors 280 to a respective given one of the outputs of a control device (not shown). The lead 260 further includes the pulse generator 180 and microcontroller 270 and the electrode selection circuit 200 within the interface portion 268. The pulse generator 180 is responsive to the power and control signals of the control device to generate the stimulation energy. The electrode selection circuit 200 is coupled to the pulse generator 180 and further has a plurality of outputs 242. Each of the outputs 242 of the electrode selection circuit 200 is coupled to a respective one of the electrodes 275 of the electrode array 264. The electrode selection circuit 200 is arranged to provide selected ones of the electrodes 275 with the stimulation energy responsive to the control signals from the control device. The plurality of outputs 242 of the electrode selection circuit 200 are greater in number than the plurality of outputs of the control device (and thus the number of contacts 284).

The lead 260 may be fabricated in the same manner as that described with respect to FIG. 6. Also, the proximal portion 266 and interface portion 268 may be fabricated without an electrode array so that together they may form a universal lead module having a pulse generator 180 therein for use with any desired electrode array. Further, as in the previous embodiments, the electrode array 264 may include a flexible substrate 288 and the electrodes 275 of the electrode array 264 may be distributed and carried on the flexible substrate 288. The flexible substrate 288 may be configured as a cylinder. The electrode array may include a flexible cylindrical carrier 289, and the flexible substrate 288 may be wrapped about the flexible cylindrical carrier. The flexible cylindrical carrier 289 may be formed of silicone.

The electrode array 264 may include a backing layer as shown in the embodiment of FIGS. 3 and 4 arranged in a corkscrew configuration. The flexible substrate 288 may be carried on the backing layer 98 within the corkscrew configuration.

While particular embodiments of the present invention have been shown and described, modifications may be made, and it is therefore intended in the appended claims to cover all such changes and modifications which fall within the true spirit and scope of the invention as defined by those claims.

What is claimed is:

1. A stimulation lead for providing stimulation energy to selected ones of a plurality of electrodes of an electrode array under control of a control device having a plurality of outputs that provide power and control signals, the stimulation lead comprising:

a flexible body and the electrode array, the electrode array being distal to the flexible body, the flexible body having a proximal portion and an interface portion;

a plurality of conductors extending through the proximal portion to the interface portion;

a connector arranged to connect a proximal end of each one of the conductors to a respective given one of the outputs;

a single pulse-generator circuit within the interface portion, the pulse-generator circuit being responsive to the power and control signals of the control device to generate the stimulation energy, the pulse-generator circuit having at least one output; and a selection circuit also within the interface portion, the selection circuit being coupled to the at least one output of the pulse-generator circuit and further having a plurality of outputs, each output of the selection circuit being coupled to a respective one of the electrodes of the electrode array and arranged to provide selected ones of the electrodes with the stimulation energy responsive to the control signals from the control device, wherein, the plurality of outputs of the selection circuit are greater in number than the plurality of outputs of the control device.

2. The stimulation lead of claim 1, wherein the electrode array includes a flexible substrate and wherein the electrodes of the electrode array are distributed and carried on the flexible substrate.

3. The stimulation lead of claim 2, wherein the flexible substrate is configured as a cylinder.

4. The stimulation lead of claim 3, wherein the electrode array includes a flexible cylindrical carrier, and wherein the flexible substrate is wrapped about the flexible cylindrical carrier.

5. The stimulation lead of claim 4, wherein the flexible cylindrical carrier is formed of silicone.

6. The stimulation lead of claim 1, wherein the selection circuit includes a switching array.

7. The stimulation lead of claim 6, wherein the switching array comprises an integrated circuit.

8. The stimulation lead of claim 1, wherein the pulse-generator circuit comprises an integrated circuit.

9. A universal stimulation lead module for providing stimulation energy to selected ones of a plurality of electrodes of an electrode array under control of a control device having a plurality of outputs that provide power and control signals, comprising:

a flexible body having a proximal portion and a distal interface portion;

a plurality of conductors extending through the proximal portion to the interface portion;

a connector arranged to connect a proximal end of each one of the conductors to a respective given one of the outputs of the control device;

a single pulse-generator circuit within the interface portion, the pulse-generator circuit having at least one output and being responsive to the power and controls signals from the control device to generate the stimulation energy; and a selection circuit also within the interface portion, the selection circuit being coupled to the at least one output of the pulse-generator circuit and further having a plurality of outputs, each output of the selection circuit being coupled to a respective one of the electrodes of the electrode array and arranged to provide selected ones of the electrodes with the stimulation energy responsive to the control signals from the control device, wherein, the plurality of outputs of the selection circuit are greater in number than the plurality of outputs of the control device.

10. The lead module of claim 9, wherein the selection circuit includes a switching array.

11. The lead module of claim 10, wherein the switching array comprises an integrated circuit.

12. The lead module of claim 9, wherein the pulse-generator circuit comprises an integrated circuit.

* * * * *